United States Patent
Tu et al.

(10) Patent No.: US 12,429,406 B2
(45) Date of Patent: Sep. 30, 2025

(54) AGENT FOR CRYOPRESERVATION AND METHOD FOR CRYOPRESERVATION OF MITOCHONDRIA USING THE SAME

(71) Applicant: TAIWAN MITOCHONDRION APPLIED TECHNOLOGY CO., LTD., Zhubei (TW)

(72) Inventors: Chi-Tang Tu, Zhubei (TW); Szu-Ting Liu, Zhubei (TW); Li-Hsin Yao, Zhubei (TW); Han-Chung Cheng, Zhubei (TW)

(73) Assignee: TAIWAN MITOCHONDRION APPLIED TECHNOLOGY CO., LTD., Zhubei (TW)

( * ) Notice: Subject to any disclaimer, the term of this patent is extended or adjusted under 35 U.S.C. 154(b) by 609 days.

(21) Appl. No.: 17/897,011

(22) Filed: Aug. 26, 2022

(65) Prior Publication Data

US 2023/0003625 A1 Jan. 5, 2023

Related U.S. Application Data

(63) Continuation-in-part of application No. PCT/CN2020/077063, filed on Feb. 28, 2020.

(51) Int. Cl.
*G01N 1/42* (2006.01)
*A01N 1/125* (2025.01)

(52) U.S. Cl.
CPC ............... *G01N 1/42* (2013.01); *A01N 1/125* (2025.01)

(58) Field of Classification Search
CPC .................................. G01N 1/42; A01N 1/125
See application file for complete search history.

(56) References Cited

U.S. PATENT DOCUMENTS

| 2004/0185524 A1 | 9/2004 | Crowe et al. |
| 2019/0184004 A1* | 6/2019 | Livengood ............. A61P 31/14 |

FOREIGN PATENT DOCUMENTS

| CN | 109789200 A | 5/2019 | |
| CN | 110684817 A | 1/2020 | |
| TW | 202023382 A * | 7/2020 | ............ A01N 1/02 |
| WO | WO-2021168764 A1 * | 9/2021 | ........... A01N 1/0221 |

OTHER PUBLICATIONS

Yamaguchi 2007 Cell Death and Differentiation, vol. 14, pp. 616-624 (Year: 2007).*
Cell Death and Differentiation, vol. 14, pp. 616-624 (Year: 2007).*

* cited by examiner

*Primary Examiner* — Mark L Shibuya
(74) *Attorney, Agent, or Firm* — Seed Intellectual Property Law Group LLP

(57) ABSTRACT

An agent for cryopreservation includes trehalose, HEPES and serum albumin. The agent for cryopreservation does not include potassium chloride, sodium chloride, ethylene glycol, ethylene glycol tetraacetic acid and ethylenediaminetetraacetic acid.

16 Claims, 3 Drawing Sheets

Embodiment

Comparative example 1

Comparative example 2

AGENT FOR CRYOPRESERVATION AND METHOD FOR CRYOPRESERVATION OF MITOCHONDRIA USING THE SAME

CROSS-REFERENCE TO RELATED APPLICATIONS

This application is a continuation-in-part of International Application No. PCT/CN2020/077063, filed Feb. 28, 2020, the entire contents of which are hereby incorporated by reference.

BACKGROUND

1. Technical Field

The present disclosure is related to an agent and a method for cryopreservation, more particularly to an agent and a method for cryopreservation of mitochondria.

2. Related Art

Mitochondria (called "mitochondrion" in singular form) are places where oxidative phosphorylation (OXPHOS) and adenosine triphosphate (ATP) synthesis occur. Since ATP is used as a source of energy in a cell, the mitochondria are described as the powerhouse of the cell. In addition to generate energy required by the cell, the mitochondria also participate in cell division, cell signaling and apoptosis of the cell, and the mitochondria has the ability to control the cell-division cycle. Since mitochondria are quite important organelles in the human body, problems with their function fail may result in diseases such as mitochondrial encephalomyopathy, and the neurodegenerative disease such as Parkinson's disease.

For these mitochondrial diseases, mitochondrial transplantation is one of the therapies. By preservation of healthy mitochondria, the healthy mitochondria can be transplanted into cells to replace the damaged mitochondria when mitochondrial diseases are found, thereby relieving the symptoms of mitochondrial diseases.

Due to a bilayer membrane structure in a mitochondrion, mitochondria are more fragile than cells. Although a variety of cryoprotectants for cells have been developed, these cryoprotectants are not suitable for the cryopreservation of mitochondria. As to the cryopreservation of mitochondria by using conventional cryoprotectants for cells, mitochondria often become swollen or even broken, resulting in the inability of mitochondria to function properly after thawing. The prevention of damage to mitochondria during cryopreservation has become an important issue, so that there is a demand of cryoprotectants specialized to the cryopreservation of mitochondria.

SUMMARY

According to one aspect of the present disclosure, an agent for cryopreservation includes trehalose, HEPES (4-(2-hydroxyethyl)-1-piperazineethanesulfonic acid) and serum albumin (SA). The agent for cryopreservation does not include potassium chloride (KCl), sodium chloride (NaCl), ethylene glycol, ethylene glycol tetraacetic acid (EGTA) and ethylenediaminetetraacetic acid (EDTA).

According to another aspect of the present disclosure, an agent for cryopreservation consists of trehalose, HEPES and SA.

According to one aspect of the present disclosure, a method for cryopreservation of mitochondria includes: providing the aforementioned agent for cryopreservation into a container; cooling down the agent for cryopreservation and the mitochondria in the container; and preserving the agent for cryopreservation and the mitochondria in the container which have been cooled down.

DETAILED DESCRIPTION

Figure 1:
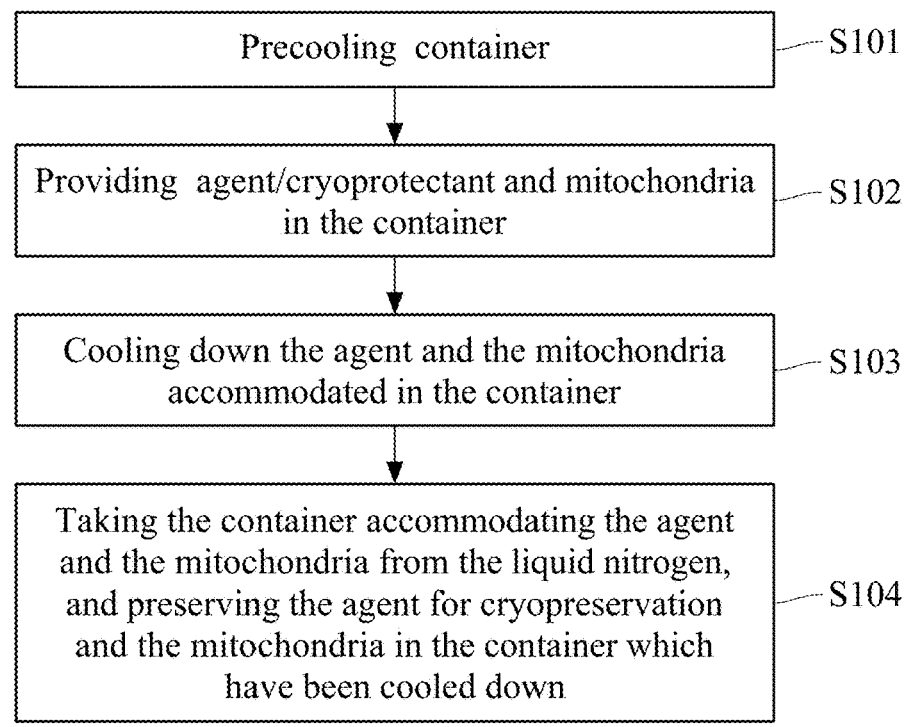
FIG. 1 is a flow chart illustrating a method for cryopreservation of mitochondria according to one embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

According to one embodiment of the present disclosure, an agent for cryopreservation includes trehalose with a molar concentration of 150 mM to 300 mM, HEPES (4-(2-hydroxyethyl)-1-piperazineethanesulfonic acid) with a molar concentration of 10 mM to 20 mM, and serum albumin (SA) with a mass percentage concentration of 0.1% to 1%. The agent for cryopreservation does not include potassium chloride (KCl), ethylene glycol, ethylene glycol tetraacetic acid (EGTA) and ethylenediaminetetraacetic acid (EDTA). In other words, an agent for cryopreservation according to one embodiment of the present disclosure may include trehalose, HEPES and SA, wherein a molar concentration of the trehalose in the agent is from 150 mM to 300 mM, a molar concentration of the HEPES in the agent is from 10 mM to 20 mM, and a mass percentage concentration of the SA in the agent is from 0.1% to 1%; and the agent for cryopreservation may not include KCl, ethylene glycol, EGTA and EDTA. The agent for cryopreservation can be used for preparation of a cryoprotectant for cryopreservation of mitochondria, such as a cryoprotectant for cryopreservation of mitochondria obtained from mammal cells. The mammal cells, for example, are human cells. In one embodiment, the agent for cryopreservation does not include sodium chloride NaCl, KCl, ethylene glycol, EGTA and EDTA.

Referring to cryopreservation, the trehalose in the agent can protect mitochondrial membrane to main integrity of a mitochondrion and normal function of the mitochondrial membrane. The HEPES in the agent can keep pH of the cryoprotectant at a nearly constant value, and HEPES can also make the cryoprotectant as an isotonic solution for mitochondria. The SA in the agent can keep constant osmotic pressure of the cryoprotectant and that of the mitochondria. In some embodiments, the SA may be derived from an individual which is the same species as one in which the mitochondria are designated to be cryopreserved; for example, human serum albumin (HSA) is selected for the cryopreservation of human mitochondria, and dog serum albumin (DSA) is selected for the cryopreservation of canine mitochondria. In some other embodiments, the SA may be derived from an individual which belongs different species from one in which the mitochondria are designated to be cryopreserved.

Referring to a conventional cryoprotectant, KCl therein is provided for adjusting the cryoprotectant to be a buffer solution and isotonic solution for mitochondria. Also, EGTA and EDTA in the conventional cryoprotectant can capture calcium ions which are generated when cell are damaged so as to prevent a large amount of calcium ions from entering the mitochondria to thereby cause changes in mitochondrial membrane permeability which may result in mitochondrial swelling or even lysis.

However, compared to the conventional cryoprotectant, the cryoprotectant according to the present disclosure does not include KCl, ethylene glycol, EGTA and EDTA. In a case that there is no KCl, ethylene glycol, EGTA and EDTA, the mitochondria cryopreserved by using the cryoprotectant of the present disclosure can enjoy better integrity and ATP synthesis ability. Therefore, the cryopreserved mitochondria maintain better function after they are thawed, which in turn leads to better performance in subsequent usage.

An embodiment of the present disclosure provides an agent for cryopreservation consists of trehalose with a molar concentration of 150 mM to 300 mM, HEPES with a molar concentration of 10 mM to 20 mM, and SA with a mass percentage concentration of 0.1% to 1%. In other words, an agent for cryopreservation according to one embodiment of the present disclosure may consist of trehalose, HEPES and SA, wherein a molar concentration of the trehalose in the agent is from 150 mM to 300 mM, a molar concentration of the HEPES in the agent is from 10 mM to 20 mM, and a mass percentage concentration of the SA in the agent is from 0.1% to 1%.

The efficacy of the elements of the agent in this embodiment and the effectiveness of the agent for preparation a cryoprotectant for cryopreservation of mitochondria are as described in the aforementioned embodiment, and will not be repeated hereafter.

According to the two embodiments mentioned above, the molar concentration of the trehalose is from 150 mM to 300 mM, preferably 200 mM to 300 mM, more preferably 250 mM to300 mM. The molar concentration of the HEPES is from 10 mM to 20 mM, preferably 10 mM to 16 mM, more preferably 10 mM to13 mM. The mass percentage concentration of the SA is from 0.1% to 1%, preferably 0.1% to 0.7%, more preferably 0.1% to 0.3%.

According to some other embodiments of the present disclosure, a ratio of the molar concentration of the trehalose to that of the HEPES (trehalose/HEPES) may be from 13 to 17, preferably 14 to 16, more preferably 15.

According to some other embodiments of the present disclosure, the agent for cryopreservation is aqueous and can be used directly, and the solvent used herein may be deionized water, but the present disclosure is not limited thereto. According to some other embodiments of the present disclosure, the agent for cryopreservation is solid, and the solid agent should be firstly prepared into liquid form with pure water (e.g., deionized water) or other solvent acceptable to the cell to be ready for use. As to the solid agent for cryopreservation, a weight ratio among dried trehalose, dried HEPES and dried serum albumin may be represented by X:Y:Z, in which X is from 92.42 to 112.96, Y is from 2.14 to 2.62, and Z is from 0.9 to 1.1; preferably, X:Y:Z is 102.69:2.38:1.

A method for cryopreservation of mitochondria according to one embodiment of the present disclosure is described as follows. Please refer to FIG. 1 showing a flow chart illustrating a method for cryopreservation of mitochondria according to one embodiment of the present disclosure. A method for cryopreservation of mitochondria may be applied to the cryopreservation of mitochondria obtained from mammal cells, such as human cells, and the method may include the following steps.

In a first step S101, the container is precooled.

In detail, the container may be placed in liquid nitrogen for precooling for 20 seconds to 40 seconds. The container may be test tube, centrifuge tube or vial.

Next, in a second step S102, the agent (or cryoprotectant) and mitochondria are provided in the container.

In detail, the precooled container is rewarmed at room temperature for 5 seconds to 15 seconds, and then the aforementioned agent of the present disclosure as well as the mitochondria are placed into the bottom of the container. When the agent and the mitochondria have been placed in the container, an operator can tap the container to aggregate the agent and the mitochondria to the bottom of the container, which prevents mitochondria residues on the inner wall of the container. The mitochondria residues on the inner wall of the container may be not rinsed with the agent for cryopreservation, so that these residual mitochondria easily swell or break during cryopreservation because they are not protected by the agent.

In a third step S103, the agent and the mitochondria accommodated in the container is cooled down.

In detail, the container accommodating the agent and the mitochondria may be placed in liquid nitrogen for 5 seconds to 15 seconds for cooling, and the agent and the mitochondria in the container are in a frozen state after cooling.

In a fourth step S104, the container accommodating the agent and the mitochondria is taken from the liquid nitrogen, and the agent for cryopreservation and the mitochondria in the container, which have been cooled down, are preserved.

In detail, the container accommodating the agent and the mitochondria may be taken from the liquid nitrogen, and the container as well as the cooled agent and mitochondria accommodated therein may be placed in a refrigerator for cryopreservation at a temperature of −70° C. to −90° C.

When someone wants to thaw the cryopreserved mitochondria, the container containing the agent and frozen mitochondria is taken from the refrigerator, and is thawed by gently shaking for 45 seconds to 65 seconds in warm water at 25° C. to 35° C. After the agent and the mitochondria in the container are completely thawed, the container with the agent and the mitochondria are inserted into crushed ice pool to keep the mitochondria at 4° C. to 10° C. for subsequent usage. An example of said subsequent usage is the use of mitochondria for mitochondrial transplantation to treat mitochondrial-related diseases.

According to the method for cryopreservation of mitochondria in the present disclosure, the thawed mitochondria, even though they were cryopreserved, can enjoy better integrity and ATP synthesis ability. Therefore, the cryopreserved mitochondria maintain better function after they are thawed, which in turn leads to better performance in subsequent usage.

The following demonstrates the effect of improved integrity and ATP synthesis ability of the mitochondria cryopreserved by using the agent (or cryoprotectant) of the present disclosure.

The following experiment is conducted by using mitochondria obtained from human stem cells. The stem cells can be prepared in a flask with a medium including 10 wt % fetal bovine serum (FBS) and cultured for 168 hours to be ready for use. The stem cells may be embryonic stem cells, induced stem cells, amniotic mesenchymal stem cells, placental mesenchymal stem cells, chorionic mesenchymal stem cells, umbilical cord mesenchymal stem cells, adipose derived stem cells (ADSC), bone marrow mesenchymal stem cells, or other sources of adult stem cells.

The mitochondria used in the experiment are prepared as follows. Firstly, about a mount of $10^8$ to $10^9$ ADSCs are taken from the cell-culture dish. Next, the ADSCs are loaded into test tube with mitochondria isolation buffer (Ibc: 225 mM mannitol, 75 mM sucrose, 30 mM Tris-HCl, pH 7.4), and the ADSCs are homogenized with the buffer by using gentleMACS™ dissociator. The broken ADSCs are placed in Percoll at a volume percentage of 30%, and the precipitate is removed by ultra-high speed centrifugation at 95,000 g for 30 minutes (min), followed by high speed centrifugation at 13,000 g for 10 min to isolate precipitated mitochondria. Then, the isolated mitochondria were rinsed with mitochondrial protein separation buffer for subsequent experiments.

The cryopreservation of the mitochondria is described as follows. Firstly, centrifuge tubes are pre-cooled in liquid nitrogen for 30 seconds. Next, the centrifuge tube are taken from the liquid nitrogen and rewarmed at room temperature for 10 seconds. Next, 300 micrograms (μg) of mitochondria which have been isolated from stem cells and 60 microliters (μL) of agent (or cryoprotectant) are placed into the space at the bottom of the centrifuge tube. Next, each tube is slightly tapped to ensure that the mitochondria and the agent are aggregated at the bottom of the tube. Next, the centrifuge tubes containing the mitochondria and the agent are placed in liquid nitrogen and allowed to stand for 10 seconds to bring the mitochondria and agent into a frozen state. Finally, the centrifuge tubes with frozen mitochondria and agent are placed in a refrigerator with an internal temperature of −80° C. for cryopreservation.

The aforementioned agent or cryoprotectant used in the method for cryopreservation of mitochondria may be selected from an embodiment of the present disclosure, a comparative example 1 or a comparative example 2. The compositions of the agents of an embodiment of the present disclosure (EM), a comparative example 1 (CE1) and a comparative example 2 (CE2) are listed in Table I.

TABLE I

|  | EM | CE1 | CE2 |
|---|---|---|---|
| trehalose | 300 mM | 300 mM | 300 mM |
| HEPES | 10 mM | 10 mM | — |
| SA | 0.1 wt % | 0.1 wt % | 0.1 wt % |
| KCl | — | 10 mM | — |
| EGTA | — | 1 mM | — |
| EDTA | — | 1 mM | — |

The method for thawing cryopreserved mitochondria is described as follows. Firstly, the centrifuge tubes containing cryopreserved mitochondria and the agent are taken from the refrigerator, and the centrifuge tubes containing cryopreserved mitochondria and the agent are immediately rinsed with warmed water bath at 30° C. The centrifuge tubes are gently shaken for 55 seconds during the warm water bath. After the mitochondria and the agent in the centrifuge tubes are completely thawed, the centrifuge tubes are placed into crushed ice pool for subsequent usage.

Next, the integrity of thawed mitochondria that have been cryopreserved for 3 months by using the agent selected from EM, CE1 or CE2 is evaluated by SEM. The thawed mitochondria are taken from the centrifuge tubes, rinsed with PBS (Phosphate buffered saline), and then made into specimens for SEM.

Figure 2:
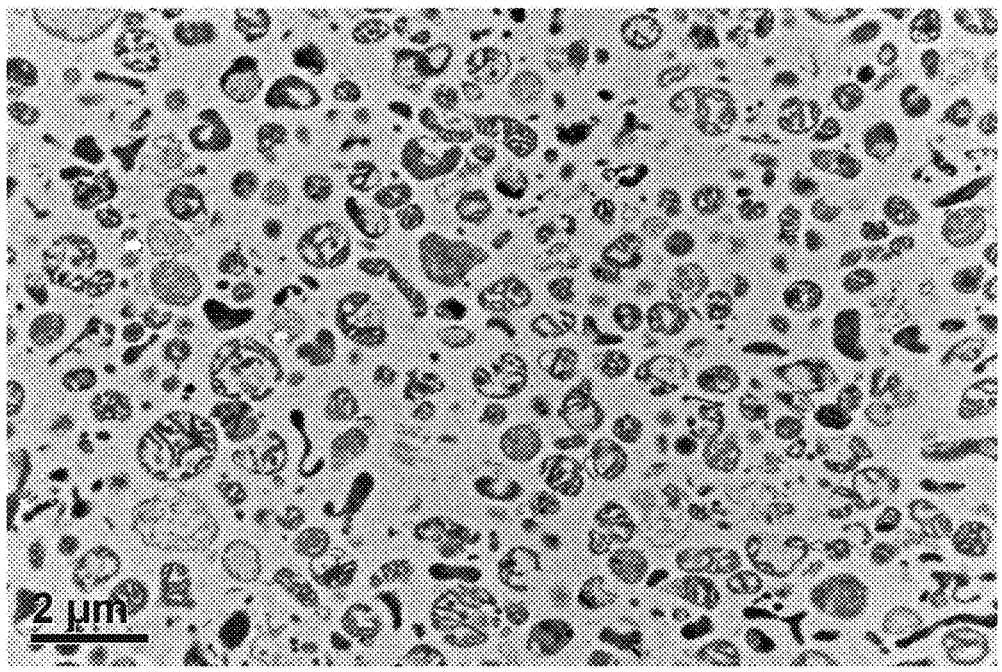
FIG. 2 is a SEM image showing thawed mitochondria after 3 months cryopreservation by using a cryoprotectant according to one embodiment of the present disclosure.
Figure 3:
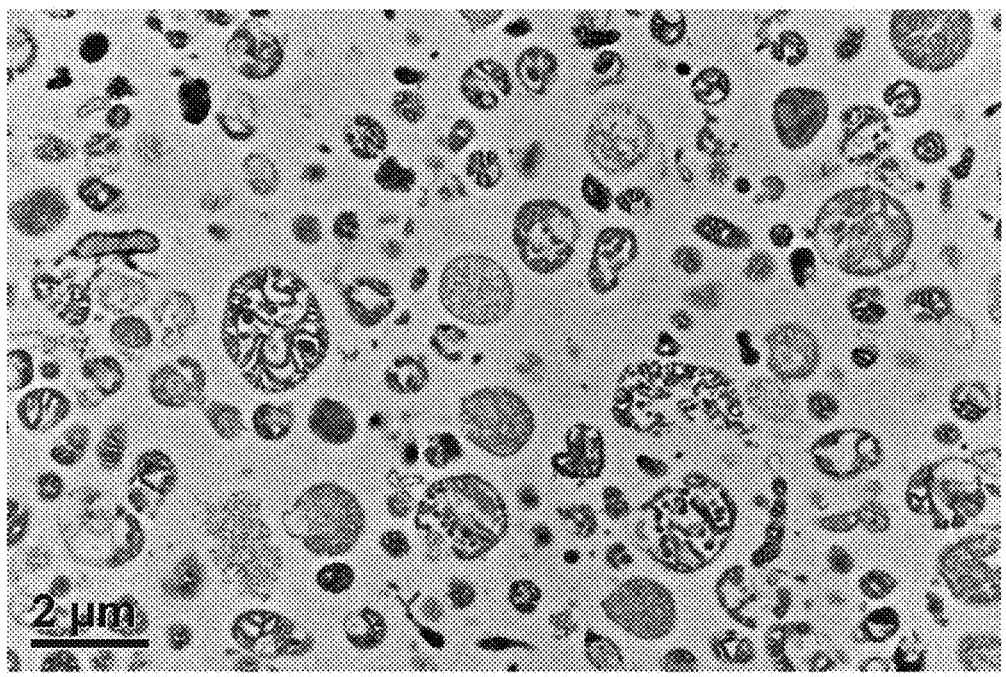
FIG. 3 is a SEM image showing thawed mitochondria after 3 months cryopreservation by using a cryoprotectant according to a first comparative example.
Figure 4:
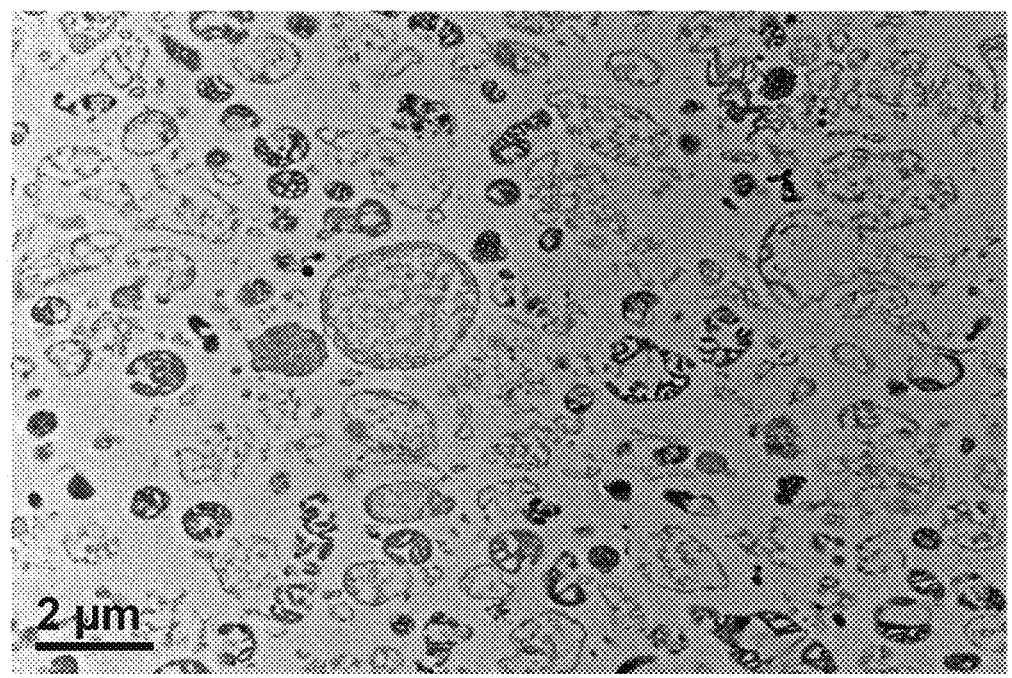
FIG. 4 is a SEM image showing thawed mitochondria after 3 months cryopreservation by using a cryoprotectant according to a second comparative example.

The SEM images are shown in FIG. 2 through FIG. 4. FIG. 2 is a SEM image showing thawed mitochondria after 3 months cryopreservation by using an agent/cryoprotectant according to one embodiment of the present disclosure. FIG. 3 is a SEM image showing thawed mitochondria after 3 months cryopreservation by using an agent/cryoprotectant according to a first comparative example. FIG. 4 is a SEM image showing thawed mitochondria after 3 months cryopreservation by using an agent/cryoprotectant according to a second comparative example.

It can be observed that a large amount of undamaged mitochondria is presented in FIG. 2, accompanied with small average diameter of the undamaged mitochondria and sharp (clear) cristae (Mitochondrial cristae) of the inner mitochondrial membrane. In contrast, a small amount of undamaged mitochondria and large average diameter of the undamaged mitochondria can be observed in FIG. 3. A very small amount of undamaged mitochondria and very large average diameter of the undamaged mitochondria can be observed in FIG. 4. Thus, as can be seen from FIG. 2 through FIG. 4, although the agent of the embodiments of the present disclosure does not include KCl, EGTA or EDTA, the mitochondria cryopreserved by using the agent of the present disclosure keep good integrity after thawing and do not suffer high average diameter as well as poor integrity due to the lack of KCl, EGTA or EDTA.

The ATP synthesis ability of the thawed mitochondria after 1 month and 3 months cryopreservation by using the agent selected from EM, CE1 or CE2 is measured by a Seahorse XF analyzer. The thawed mitochondria are taken from the centrifuge tubes, rinsed with PBS, and then assayed with the Seahorse XF analyzer.

The Seahorse XF analyzer measures ATP synthesis ability of the thawed mitochondria by the following steps: 20 μg of mitochondria are placed in the analytical wells with analytical medium, and then the basal oxygen consumption rate in the mitochondria is detected. Then, some amount of ADP is added into the wells as the material for ATP synthesis, and the ATP synthesis oxygen consumption rate in the mitochondria is detected at this time. Then, some ATP synthesis inhibitors are added to decrease the activity of the mitochondria to synthesize ATP, and non-ATP synthesis oxygen consumption rate in the mitochondria is detected at this time. The ATP synthesis inhibitors may be oligomycin. Next, an appropriate concentration of anti-coupler is added to the wells, and the mitochondria are allowed to idle in the limiting condition without disrupting the electron transport chain of the inner mitochondrial membrane to assess oxygen consumption rate of the electron transport chain of the inner mitochondrial membrane. The anti-coupler may be carbonyl cyanide-4-(trifluoromethoxy)phenylhydrazone (FCCP). Finally, electron transport chain inhibitors are added into the wells to completely stop mitochondrial oxygen consumption, thereby determining background value of the oxygen consumption rate. The electron transport chain inhibitors may be rotenone, antimycin A or a combination thereof.

Figure 5:
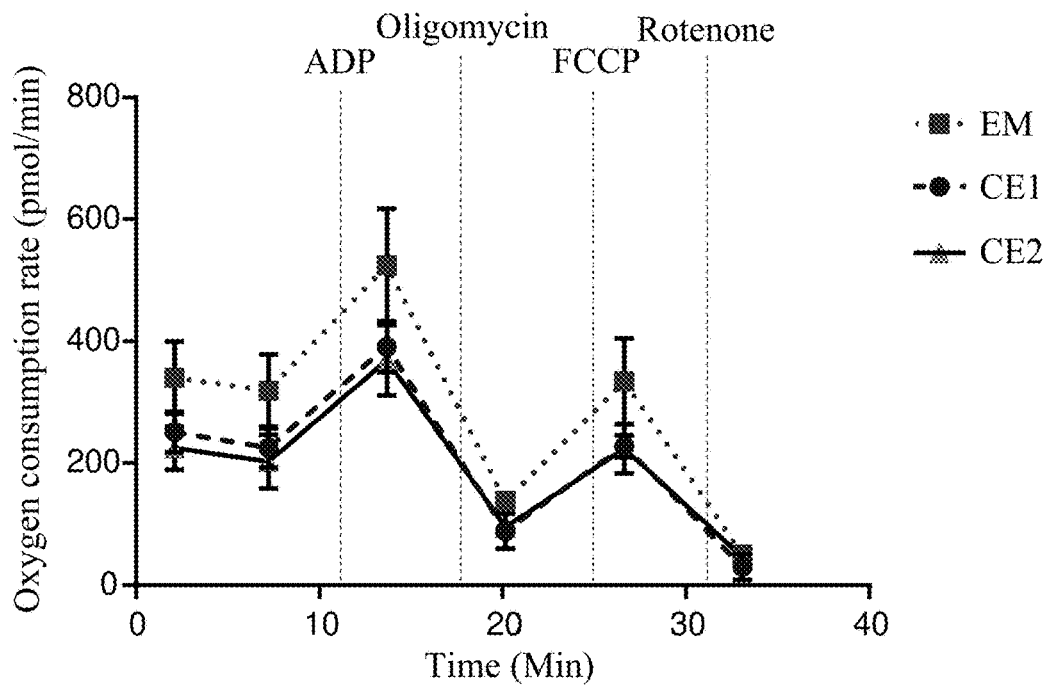
FIG. 5 is a graph showing oxygen consumption of thawed mitochondria after 1 month cryopreservation by using cryoprotectants according to one embodiment of the present disclosure and comparative examples.
Figure 6:
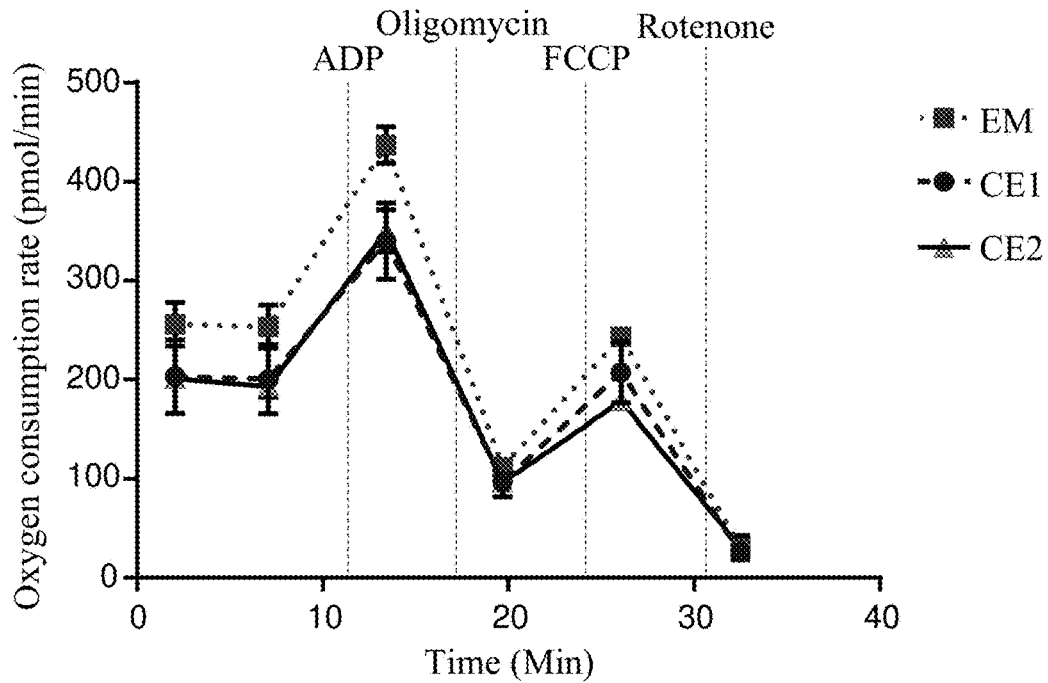
FIG. 6 is a graph showing oxygen consumption of thawed mitochondria after 3 months cryopreservation by using cryoprotectants according to one embodiment of the present disclosure and comparative examples.

Results of ATP synthesis ability measurement by the Seahorse XF analyzer are summarized in TABLE II, FIG. 5 and FIG. 6. FIG. 5 is a graph showing oxygen consumption of thawed mitochondria after 1 month cryopreservation by using agents/cryoprotectants according to one embodiment of the present disclosure and comparative examples. FIG. 6 is a graph showing oxygen consumption of thawed mitochondria after 3 months cryopreservation by using agents/cryoprotectants according to one embodiment of the present disclosure and comparative examples.

TABLE II

| | EM | | CE 1 | | CE2 | |
|---|---|---|---|---|---|---|
| | 1 month | 3 months | 1 month | 3 months | 1 month | 3 months |
| Basal oxygen consumption rate (pmol/min) | 319.1 (59.6) | 253.34 (21.84) | 225.1 (32.1) | 200.80 (35.20) | 202.1 (44.4) | 192.55 (10.64) |
| Non-ATP synthesis oxygen consumption rate (pmol/min) | 524.7 (92.0) | 437.40 (18.52) | 391.0 (41.7) | 340.11 (38.83) | 369.0 (57.9) | 350.56 (21.32) |
| ATP synthesis oxygen consumption rate (pmol/min) | 137.8 (8.9) | 112.19 (4.17) | 88.9 (27.9) | 97.40 (8.30) | 94.7 (4.5) | 96.87 (14.83) |
| Electron transport chain oxygen consumption rate (pmol/min) | 334.3 (70.7) | 243.70 (4.10) | 227.7 (18.4) | 207.11 (31.07) | 223.6 (40.5) | 178.46 (4.58) |
| Background value (pmol/min) | 50.3 (15.6) | 30.74 (9.77) | 30.2 (21.1) | 26.18 (3.15) | 46.0 (17.2) | 30.54 (11.97) |

Note:
values in parentheses are the standard deviations of the measured values.

As shown in TABLE II and FIG. 5, regarding 1 month cryopreservation, the thawed mitochondria, which were cryopreserved by using the agent of EM, have significantly higher oxygen consumption rate, higher ATP synthesis oxygen consumption rate and higher electron transport chain oxygen consumption rate that that cryopreserved by using the agents of CE1 and CE2. It can be concluded that the mitochondria cryopreserved for 1 month by using the agent of EM have better health and normal function after thawing. As shown in TABLE II and FIG. 6, regarding 3 months cryopreservation, the thawed mitochondria, which were cryopreserved by using the agent of EM, have significantly higher oxygen consumption rate, higher ATP synthesis oxygen consumption rate and higher electron transport chain oxygen consumption rate that that cryopreserved by using the agents of CE1 and CE2. It can be concluded that the mitochondria cryopreserved for 3 months by using the agent of EM have better health and normal function after thawing.

Referring to TABLE II, FIG. 5 and FIG. 6, the thawed mitochondria, which were cryopreserved by using the agent/cryoprotectant according to the present disclosure, enjoy better ATP synthesis ability. Accordingly, the thawed mitochondria, which were cryopreserved by using the agent/cryoprotectant according to the present disclosure, have a potential to be applied for (that is, more suitable) mitochondrial transplantation therapy.

According to the present disclosure, the mitochondria cryopreserved by using the agent/cryoprotectant and method of the present disclosure can enjoy better integrity and ATP synthesis ability. Therefore, the cryopreserved mitochondria maintain better function after they are thawed, which in turn leads to better performance in subsequent usage.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. An agent for cryopreservation, comprising:
    trehalose;
    HEPES; and
    serum albumin;
    wherein the agent for cryopreservation does not comprise potassium chloride, sodium chloride, ethylene glycol, ethylene glycol tetraacetic acid and ethylenediaminetetraacetic acid;
    wherein a weight ratio among the trehalose, the HEPES and the serum albumin is X:Y:Z, X is from 102.69 to 112.96, Y is from 2.14 to 2.62, and Z is from 0.9 to 1.1.

2. The agent for cryopreservation according to claim 1, wherein a molar concentration of the trehalose is 300 mM, a molar concentration of the HEPES is from 10 mM to 20 mM, and a mass percentage concentration of the serum albumin is from 0.1% to 1%.

3. The agent for cryopreservation according to claim 1, wherein a molar concentration of the trehalose is 300 mM.

4. The agent for cryopreservation according to claim 1, wherein a molar concentration of the HEPES is 10 mM.

5. The agent for cryopreservation according to claim 1, wherein a mass percentage concentration of the serum albumin is 0.1%.

6. A method for cryopreservation of mitochondria from human cells, comprising:
    providing the agent for cryopreservation according to claim 1 and mitochondria into a container;
    cooling down the agent for cryopreservation and the mitochondria in the container; and
    preserving the agent for cryopreservation and the mitochondria in the container which have been cooled down.

7. A method for cryopreservation of mitochondria, comprising:
    providing the agent for cryopreservation according to claim 1 and mitochondria into a container;
    cooling down the agent for cryopreservation and the mitochondria in the container; and preserving the agent for cryopreservation and the mitochondria in the container which have been cooled down.

8. The method for cryopreservation of mitochondria according to claim 7, further comprising: precooling the container, before providing the agent for cryopreservation and the mitochondria into the container.

9. An agent for cryopreservation, consisting essentially of trehalose, HEPES and serum albumin;
wherein a weight ratio among the trehalose, the HEPES and the serum albumin is X:Y:Z, X is from 102.69 to 112.96, Y is from 2.14 to 2.62, and Z is from 0.9 to 1.1.

10. The agent for cryopreservation according to claim 9, wherein a molar concentration of the trehalose is 300 mM, a molar concentration of the HEPES is from 10 mM to 20 mM, and a mass percentage concentration of the serum albumin is from 0.1% to 1%.

11. The agent for cryopreservation according to claim 9, wherein a molar concentration of the trehalose is 300 mM.

12. The agent for cryopreservation according to claim 9, wherein a molar concentration of the HEPES is 10 mM.

13. The agent for cryopreservation according to claim 9, wherein a mass percentage concentration of the serum albumin is 0.1%.

14. A method for cryopreservation of mitochondria from human cells, comprising:
providing the agent for cryopreservation according to claim 9 and mitochondria into a container;
cooling down the agent for cryopreservation and the mitochondria in the container; and
preserving the agent for cryopreservation and the mitochondria in the container which have been cooled down.

15. A method for cryopreservation of mitochondria, comprising: providing the agent for cryopreservation according to claim 9 and mitochondria into a container;
cooling down the agent for cryopreservation and the mitochondria in the container; and
preserving the agent for cryopreservation and the mitochondria in the container which have been cooled down.

16. The method for cryopreservation of mitochondria according to claim 15, further comprising:
precooling the container, before providing the agent for cryopreservation and the mitochondria into the container.

* * * * *